May 28, 1957 H. G. MOLINARI Re. 24,322

HYPODERMIC SYRINGE AND BARREL BLANK

Original Filed May 20, 1952

INVENTOR.
Henry G. Molinari
BY
Kane, Dalimarta & Kane
ATTORNEYS

United States Patent Office

Re. 24,322

Reissued May 28, 1957

24,322

HYPODERMIC SYRINGE AND BARREL BLANK

Henry G. Molinari, Rutherford, N. J., assignor to Becton Dickinson and Company, Rutherford, N. J., a corporation of New Jersey Original No. 2,776,661, dated January 8, 1957, Serial No. 288,780, May 20, 1952. Application for reissue March 4, 1957, Serial No. 643,901

7 Claims. (Cl. 128—218)

Matter enclosed in heavy brackets [ ] appears in the original patent but forms no part of this reissue specification; matter printed in italics indicates the additions made by reissue.

This invention relates to a structurally and functionally improved hypodermic syringe assembly as well as a barrel blank to be employed in providing such assembly.

The present application is a continuation-in-part of my prior case on "Syringe Barrel and Machine and Method for Forming the Same" filed in the United States Patent Office on June 12, 1948, and identified under Serial Number 32,660 of which a continuing application resulted in U. S. Patent No. 2,684,556.

By means of the present invention a barrel blank is furnished which is ideally suited for use in connection with the machine and method as taught in my prior [application] *patent*; this blank being capable of being employed by relatively unskilled labor to provide a unit in a syringe assembly of superior type.

It is a further object of the invention to furnish a syringe assembly which will meet all standards of the medical profession and which may be subjected to repeated cleaning and sterilizing operations, involving the use of detergents, without the assembly being detrimentally affected.

A further object is that of furnishing a hypodermic syringe in which the danger of "squirt backs" is avoided in that the parts—while being freely movable with respect to each other—will have cooperating characteristics permitting of the ejection of highly fluid medicaments despite the fact that objectional leakages are prevented.

An additional object is that of providing an assembly which will have a long effective life and which may be largely produced by automatic machinery and methods with minimum of manual supervision and final inspections.

With these and other objects in mind, reference is had to the attached sheet of drawings illustrating one practical embodiment of the invention and in which.

Figure 1:
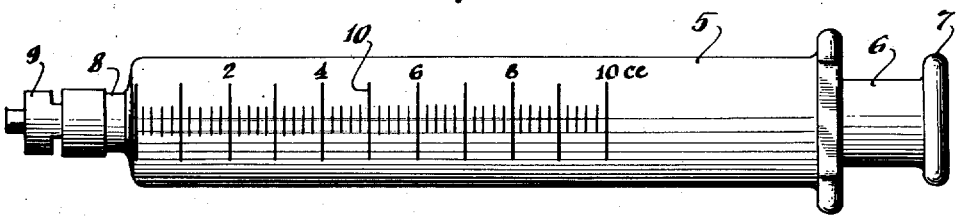
Fig. 1 is a side elevation of a complete assembly.

Referring primarily to Fig. 1, the numeral 5 indicates a glass syringe barrel within the bore of which a plunger 6 may be reciprocated. In accordance with conventional techniques, the rear of this plunger preferably terminates in a portion 7 suitable for engagement with the thumb or finger of the operator. The opposite end of the syringe barrel terminates in a tip 8. This tip conveniently mounts a fitting 9 embracing any suitable structure by means of which a hypodermic needle (not shown) may be supported on the tip. The face of the syringe preferably includes suitable indicia 10 in the form of subdivisions indicating cubic centimeters and fractions thereof. The indicia may obviously additionally include any other desired data.

Figure 2:
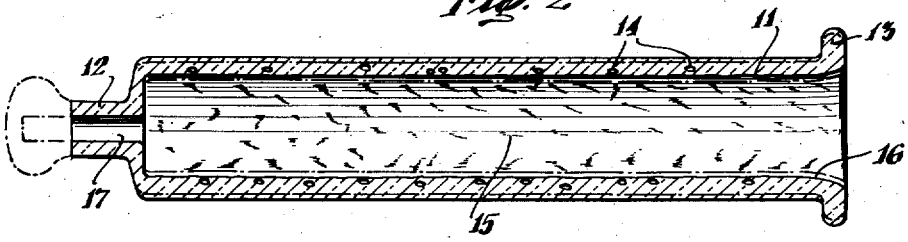
Fig. 2 is a sectional side view of a barrel blank or preform.

In accordance with the present invention the syringe barrel is formed from a blank or preform of glass. That preform embraces as shown in Fig. 2 a body 11 having adjacent one of its ends a *closing* wall continued in the form of a tip 12. As indicated in Fig. 2, this tip may be sealed or else open. Adjacent its opposite end the blank is preferably formed with an outstanding flange portion 13. The body 11 of the preform may contain minute air bubbles 14 as an incident to the initial formation of the blank. The bore 15 of the preform may be relatively rough or irregular although to assure a maximum production of perfect units it should be as nearly truly cylindrical as is practicable. Conveniently this bore is flared adjacent its rear or open end as indicated at 16. It is continued at its forward end in a passage or bore 17 extending into the tip 12. As afore brought out, that tip may either be open or sealed as indicated in Fig. 2.

Figure 3:
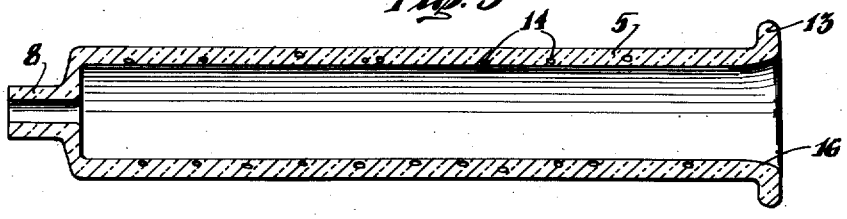
Fig. 3 is a similar view but showing the barrel in substantially completed condition.

After this preform has been mounted upon the mandrel of the machine and subjected to the forming operations as taught in my prior [application] *patent*, its bore is decreased in diameter. Likewise, its external diameter may be somewhat decreased. This has been indicated in Fig. 2 by the dot and dash lines which show the final dimensions in comparison with the full lines. For purposes of illustration, the differences in dimensions have been somewhat exaggerated as has also the showing of irregular surfaces defining the bore 15. In any event, and as illustrated in Fig. 3, a barrel 5 is produced which adjacent its open or rear end preferably includes a flange 13 with the bore flared adjacent this flange as at 16. The air bubbles 14 will remain within the body of the unit in that no grinding is necessary in accordance with the method which is practiced. Therefore, these air bubbles will not be in effect opened by the action of the grinding tool resulting in what is commonly known as "air-lines" which might render the syringe barrel unsuitable for use. Rather, the bore remains smooth and uninterrupted and presents a "chill" surface throughout its length. In other words, this surface will embody the characteristics of what might be termed very hard veneer. That surface will be quite hard and resist to a maximum extent any erosive action by strong concentrations of detergents or other substances. Thus, there is produced by the machine and method traversed in my earlier application a syringe barrel which requires only the application of a fitting to its tip if such a fitting is necessary.

Figure 4:
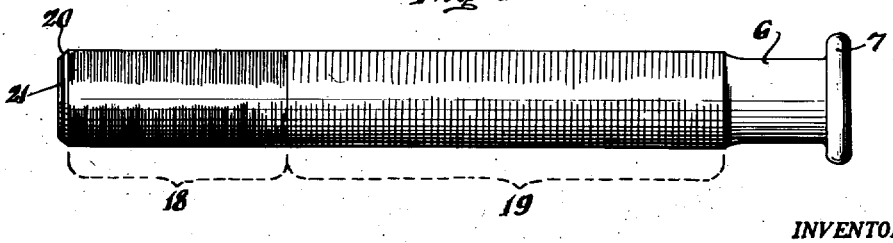
Fig. 4 is a side elevation of a plunger constructed in accordance with the present teachings and for use with that barrel.

To complete the assembly the plunger is produced. That plunger is again formed completely of glass. It is preferably provided by associating a suitably semi-completed unit with a centerless grinder so that the body of the piston or plunger has the lines of grinding and lapping extending transversely of the plunger axis. *These lines define peak portions and valleys of microscopic dimensions.* [Throughout its forward area] *Throughout the forward area of the plunger,* indicated at 18 in Fig. 4 a bearing surface is furnished which is as nearly truly cylindrical as is feasible and includes a "micro-finish" (one in which the peaks and valleys of the lines of grind vary, for example, from three to twenty .00001"). This bearing surface extends in excess of ten percent of the effective length of the plunger and conveniently includes an area of slightly in excess of thirty percent of that length. While only area 18 need be lapped, it is preferred as a practical matter to also lap area 19. The latter conveniently tapers to the right as viewed in Fig. 4 to from two to five .0001".

By having the bearing area 18 of the length specified, an adequate seal is furnished such that the plunger may be reciprocated within the bore of the barrel in a relatively free manner, but at the same time the length of the seal area will prevent leakage. Also, due to this effective area, even when the plunger is repeatedly subjected to the action of detergents, it will not be affected detrimentally. The tapered nature of area 19 assures that the plunger will freely ride within the bore of the barrel.

The forward end of the plunger is preferably tapered as indicated at 20. A line or other indicating mark 21 may be incorporated in this end portion. The walls of the barrel being transparent, the line will be readily visible through such walls. Therefore, a physician may align the end of the plunger with the desired unit or subdivision 10 and be assured that the syringe contains just the desired volume of medicament to be injected.

The plunger will have a free, sliding action within the barrel bore. The seal provided between the ground and lapped surface of the plunger and the smooth, clean bore face will be extremely effective. It will assure a proper explusion of liquid contained in the barrel as the plunger is projected. Due to the character of the cooperating surfaces there will be no danger of objectionable rearward leaks or "squirt-backs" between the barrel and plunger surfaces. This will also be assured by the increased area of the seal between these parts. Additionally, as a consequence of the increase in sealing area of the plunger or piston the surface of the latter will not be rendered ineffective even when repeatedly subjected to the action of concentrated detergents. Therefore, the effective life of the assembly will be much greater than has heretofore been the case.

Thus, among others, the several objects of the invention as specifically aforenoted are achieved. Obviously, numerous changes in construction and rearrangement of the parts might be resorted to without departing from the spirit of the invention as defined by the claims.

I claim:

1. A syringe barrel blank for application to a barrel-shrinking machine in which the bore diameter of said blank is decreased, the blank diameter is decreased and the length of said blank remains substantially unchanged, said blank including a tubular body of a length substantially equal to that to be embraced in the finished barrel, said body having an unground, substantially cylindrical bore having relatively raised and lowered portions on its surface, the diameter of such bore being substantially larger than that to be incorporated in the finished syringe, a flange adjacent one end of said body and extending outwardly therefrom, a closed end of said bore forming an end wall closing the opposite end of said body and a needle mounting tip extending beyond said end wall.

2. A syringe barrel blank for application to a barrel-shrinking machine in which the bore diameter of said blank is decreased, the blank diameter is decreased and the length of said blank remains substantially unchanged, said blank including a tubular body of a length substantially equal to that to be embraced in the finished barrel, said body having an unground, substantially cylindrical bore having relatively raised and lowered portions on its surface, the diameter of such bore being substantially larger than that to be incorporated in the finished syringe, a flange adjacent one end of said body and extending outwardly therefrom, a closed end of said bore forming an end wall closing the opposite end of said body, a needle mounting tip extending beyond said end wall, said tip being formed with a passage and material integral with said tip for sealing the outer end of said passage.

3. A syringe assembly including in combination a barrel presenting a smooth and cylindrical unground bore of uniform diameter throughout its effective length to thus embrace in the bore face a smooth uninterrupted surface [embracing peak portions and valleys] and a plunger reciprocable in said bore and having a lapped cylindrical bearing surface *embracing peak portions and valleys cooperating* with the inner surface of said barrel, the peak portions of the grind in such surface being in sealing contact with said bore surface.

4. A syringe assembly including in combination a barrel presenting a smooth and cylindrical unground bore of uniform diameter throughout its effective length to thus embrace in the bore face a smooth uninterrupted surface [embracing peak portions and valleys] and a plunger reciprocable in said bore and having a lapped cylindrical bearing surface *embracing peak portions and valleys cooperating* with the inner surface of said barrel, the peak portions of the grind in such surface being in sealing contact with said bore surface, said lines of grind extending transversely to the axis of said plunger.

5. A syringe assembly including in combination a barrel presenting a smooth and cylindrical unground bore of uniform diameter throughout its effective length to thus embrace in the bore face a smooth uninterrupted surface [embracing peak portions and valleys] and a plunger reciprocable in said bore and having a lapped cylindrical bearing surface *embracing peak portions and valleys cooperating* with the inner surface of said barrel, the peak portions of the grind in such surface being in sealing contact with said bore surface, and the length of said bearing surface being not less than ten percent of the effective length of said plunger.

6. A syringe assembly including in combination a barrel presenting a smooth and cylindrical unground bore of uniform diameter throughout its effective length to thus embrace in the bore face a smooth uninterrupted surface [embracing peak portions and valleys] and a plunger reciprocable in said bore and presenting a lapped cylindrical bearing surface *embracing peak portions and valleys*, the peak portions of the grind in such surface being in sealing contact with said bore surface and the effective length of said bearing surface being substantially thirty percent of the effective length of said plunger.

7. A syringe assembly including in combination a barrel presenting a completely smooth and cylindrical bore of uniform diameter throughout its effective length to thus embrace in the bore face a smooth uninterrupted surface, a plunger having an inner end reciprocable in said bore and having a lapped cylindrical bearing surface embracing peak portions and valleys, the peak portions of the grind in such surface extending transversely of the plunger axis and being in sealing contact with said bore surface adjacent the inner plunger end and the effective length of said bearing surface being substantially thirty percent of the effective length of said plunger.

References Cited in the file of this patent or the original patent

UNITED STATES PATENTS

| | | |
|---|---|---|
| 772,450 | Wulfing-Luer | Oct. 18, 1904 |
| 1,863,785 | Dickinson | June 21, 1932 |
| 2,392,104 | Smith | Jan. 1, 1946 |
| 2,641,093 | Kolodny et al. | June 9, 1953 |

FOREIGN PATENTS

| | | |
|---|---|---|
| 2,130 | Great Britain | Jan. 30, 1908 |